United States Patent [19]

Berg et al.

[11] Patent Number: 4,820,919
[45] Date of Patent: Apr. 11, 1989

[54] METHOD OF DETERMINING THE DENSITY OF SUBSTRATA

[75] Inventors: Flemming Berg, Skovlunde; Povl L. Ølgaard, Roskilde; John L. Jørgensen, Kastrup, all of Denmark

[73] Assignee: Statens Vejlaboratorium, Denmark

[21] Appl. No.: 205,610

[22] Filed: Jun. 6, 1988

Related U.S. Application Data

[63] Continuation of Ser. No. 863,705, May 15, 1986.

[30] Foreign Application Priority Data

May 28, 1985 [DK] Denmark .............................. 60-2377

[51] Int. Cl.$^4$ ........................ G01N 9/24; G01N 23/02; G01V 5/12
[52] U.S. Cl. .................................. 250/269; 250/256; 250/358.1; 378/89
[58] Field of Search ............... 250/358.1, 360.1, 505.1, 250/256, 266, 269; 378/54, 55, 56, 89

[56] References Cited

U.S. PATENT DOCUMENTS

| | | | |
|---|---|---|---|
| 3,176,134 | 3/1965 | Wright | 250/277 |
| 3,531,643 | 9/1970 | Bretonniere et al. | 378/54 |
| 4,034,218 | 7/1977 | Turcotte | 250/269 |
| 4,048,495 | 9/1977 | Ellis | 250/266 |
| 4,529,877 | 7/1985 | Arnold | 250/256 |

OTHER PUBLICATIONS

Jorgensen et al., "Density Measurements by Means of Once Scattered Gamma Radiation, The ETG Probe, Principles, and Equipment" from Dept. of Electrophysics, Technical University of Denmark, National Road Laboratory 1987.

Primary Examiner—Janice A. Howell
Assistant Examiner—William F. Rauchholz
Attorney, Agent, or Firm—Scully, Scott, Murphy & Presser

[57] ABSTRACT

A method for determining the density of substrata by means of a radiation source K comprising a collimator (1) and of a detector comprising a collimator (3), by which method the direction of radiation may optionally be changed in relation to the direction of detection, and the change of the detected signal may be measured. According to the invention the direction of radiation and the direction of detection are situated in substantially the same plane. By deducting the signal of the desirable depth of measurement from a somewhat greater depth of measurement, substantially only the signal originating from singly scattered radiation is obtained, and as a result it will be possible to measure the density at greater depth than previously. On the basis of a spectrum analysis of the spectrum originating from the measurement, the variation of the density with the depth could be obtained.

2 Claims, 3 Drawing Sheets

METHOD OF DETERMINING THE DENSITY OF SUBSTRATA

This application is a continuation of application Ser. No. 863,705, filed May 15, 1986.

BACKGROUND OF THE INVENTION

The present invention relates to a method of determining the density of substrata of a considerable thickness by means of a gamma-radiation source comprising a collimator and of a detector comprising a collimator, both located on the surface of the substratum. The direction of radiation may be changed in relation to the direction of detection, and the change of the detected signal may be measured by means of the inventive method.

FIG. 3 illustrates an arrangement performing measurements on the basis of scattered gamma-radiation. The gamma-radiation emitted from the source is collimated to a thin beam, L, of gamma-quanta, which is damped exponentially during the passage of the object under measurement, said damping being dependent on the density of the object under measurement. The damping is substantially due to Compton-scattering, and the gamma-quanta are scattered in a direction away from the beam L in all directions. Some of the scattered quanta will—optionally subsequent to additional scatterings—be directed towards the detector.

DESCRIPTION OF THE PRIOR ART

The quanta detected by the detector can be divided into the following groups:

Group A: The singly scattered quanta, which are only scattered in the reflection volume (cf. FIG. 3), and which after scattering are directed towards the detector. This group also comprises the quanta which are subjected to scatterings on its way down to the reflection volume and on its way up to the detector, but where the scattering angles in connection with all scatterings—apart from the scattering in the reflection volume—are very small. These quanta, which at the arrival at the detector have almost the same energy as the singly scattered quanta, are of great importance, as they dominate the result of measurement in connection with measurements at great depth. If the detector only detected group-A-quanta, the results of measurement would be an expression of the average density in the depth area 0 to x.

Group B: The quanta, which are subjected to two or only a few scatterings with scattering angles of a considerable size, and which reach the detector without passing the reflection volume. Such quanta may e.g. follow the way L-2-M or L-3-M. These quanta, which on the average return at a smaller depth, have an energy which on the average is somewhat greater than the energy of the quanta of group A.

Group C: The quanta, which are subjected to many scatterings usually without passing the reflection volume. These quanta have an average energy much lower than the energy of the quanta of groups A and B. However, a small portion of the quanta of group C have energies of the same order as the quanta of groups A and B.

FIG. 5 illustrates an example of a gamma-spectrum measured by the detector. However, the spectrum depends on the desired depth of measurement. If this depth x is smaller than about 10 cm, the majority of the measuring signal of the detector will originate from the quanta of group A depending on the composition and density of the material in question. When the depth of measurement is increased beyond about 10 cm, the fact that the signal from the quanta of group A is damped exponentially, whereas the signal from the quanta of groups B and C is almost constant and only to a small degree depends on the depth of the return area, will soon implicate that the detector signals are dominated by the quanta of groups B and C.

By changing the geometry in such a manner that the center line of the collimators of the source and the detector is no longer in the same plane, and the measuring signal is in principle only due to the quanta of group C. This method is described in U.S. Pat. No. 4,034,218. As illustrated in FIG. 1 of U.S. Pat. No. 4,034,218, the measuring signal will, after the described change of geometry, be entirely without the bulge originating from the quanta of groups A and B. By deducting the measuring signal after the described change of geometry from the measuring signal before the change, a signal is obtained which essentially originates from the quanta of groups A and B. For depths of measurement of less than about 10 cm this signal will as described above be dominated by quanta of group A. In connection with greater depths the quanta of group B will quickly be dominating, and the measuring signal obtained will consequently be practically independent of the depth of measurement. The method described in U.S. Pat. No. 4,034,218 is consequently not suited for measuring the density of layers of material with thicknesses of more than about 10 cm.

SUMMARY OF THE INVENTION

According to the invention of said patent specification the centerlines of the collimators of source and detector will always be in the same plane. By using for this geometrical configuration the difference between the result of measurement corresponding to the desirable depth of measurement and the result of measurement corresponding to a somewhat greater depth of measurement, a signal is obtained, which is practically only determined by the quanta of group A, which are scattered in the desirable depth of measurement. The contributions of the quanta of groups B and C will, in the two measuring signals, be of practically equal size and thus neutralize each other, whereas the contribution of the quanta of group A which are scattered at a greater depth will be very small due to the additional exponential damping, to which these quanta are subjected on account of the greater depth. This method makes it possible to measure the density at considerably greater depth than previously.

Information as to the variation of the density with the depth is furthermore obtainable on the basis of the measured gamma-spectrum.

BRIEF DESCRIPTION OF THE DRAWING

The invention will be described more detailed below with reference to the accompanying drawing, in which.

DESCRIPTION OF THE PREFERRED EMBODIMENTS

An example of the use of gamma-density measurements are described in the following.

In road building it is of great importance that the road substratum is compacted sufficiently, and considerable means are used for compacting control. It is known to perform this control by means of the so-called "sand replenishment method". By this method a 15 cm deep hole is dug, whereafter the density and the water content of the material dug up are determined by packing the hole with sand of a well-defined density and by drying the sand dug up. This method requires, however, much work. Furthermore, the result of the determination of the water content will not be available until the next day.

It is also known to use nuclear probes for determining the density and the water content of a road substratum. These probes yield a quick result with a modest performance.

The surface density of the stratum of earth is determined by means of nuclear probes either by the back-scattering method or by the transmission method.

In the usual back-scattering method (with the use of collimators) a gamma-source on the surface emits gamma-quanta into the stratum, where said quanta are scattered, whereafter they are able to reach a gamma-detector also located on the surface. The gamma-detector is shielded against direct radiation from the gamma-source. In connection with densities above about 1 g/cm$^3$, the counting velocity of the detector decreases concurrently with increasing earth density. An increased number of atoms per volume unit will prevent the gamma-quanta from reaching the detector, and simultaneously the absorption probability of the gamma-quanta will be increased. The advantage of the back-scattering method is that it does not disturb the road surface. On the other hand the usual back-scattering only indicates the density of the upper 4-6 cm, which is not sufficient in earth compacting tests.

Figure 1:
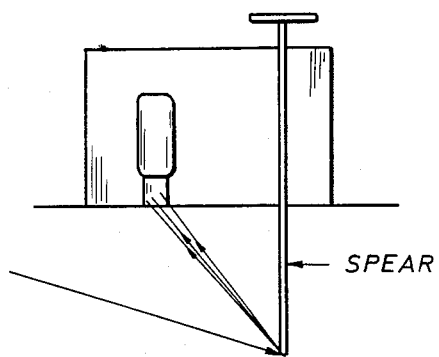
FIG. 1 illustrates a known measuring equipment comprising a probe inserted into the surface of the earth.

In the transmission method—cf. FIG. 1—a spear with a gamma-source in the head is lead 15-20 cm down into the stratum. From here the gamma-quanta of the source are able to reach the gamma-detector. The registered counting velocity depends on the damping of the stratum, which in turn is determined by the density of the stratum. The greater the density is, the lower is the counting velocity due to the greater damping. The advantage of the transmission method is that it measures the average value of the density in the earth from source to detector. The insertion of the spear may on the other hand be difficult, optionally impossible, if the stratum contains many stones, which is normally the case in connection with road building materials. The method is furthermore inapplicable, if the measurements are to be performed on e.g. asphalt, concrete or other solid materials.

The method here described is based on Compton-scattering of gamma-quanta. In the method a collimated gamma-luminous beam is emitted into the medium in question, where the gamma-quanta are scattered—cf. FIG. 2. By measuring only the quanta of group A scattered in a depth of up to about 25 cm, a counting velocity is obtained, which is a standard for the average density of the medium down to this depth. The energy of the quanta of group A is close to the value calculated by Compton's formula:

$$E_\gamma = \frac{E_o}{1 + \frac{E_o}{0.511}(1 - \cos\theta)}$$

(E in MeV)

Figure 2:
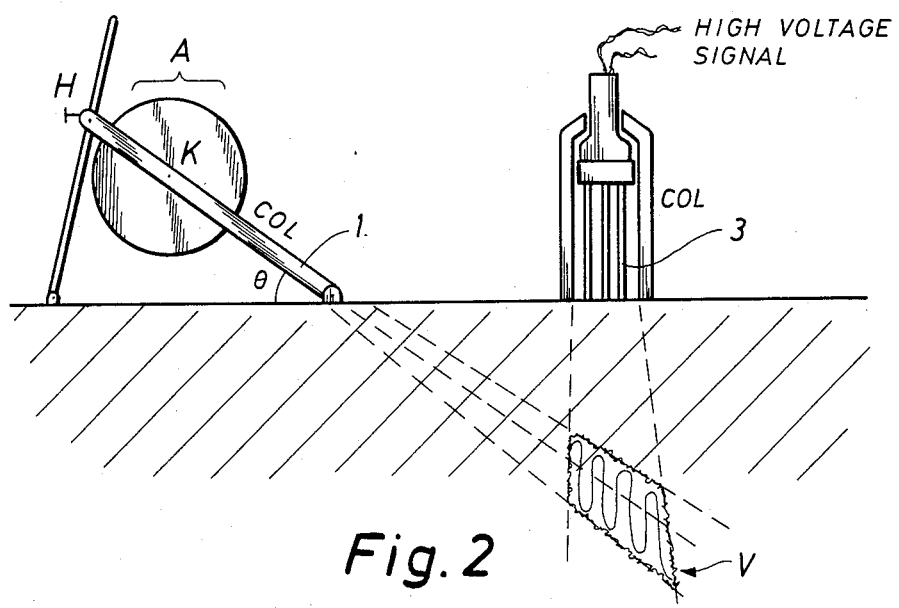
FIG. 2 illustrates a measuring equipment according to the invention.

$E_o$ is the energy of the gamma-quanta emitted by the source and $\theta$ is the angle shown in FIG. 2. This method ensures that only the quanta of group A with an energy of about $E_\gamma$ are measured.

The measuring arrangement used is as illustrated in FIG. 2. The gamma-radiation from the source K (about 30 mCi$^{137}$Cs) is emitted uniformly in all directions. The collimator of the source has an aperture angle of about $3\times6°$, whereas the collimator of the detector has an aperture angle of about $3\times8°$. The gamma-quanta will only reach the surroundings, if they are directed out through the collimator. The remaining quanta are absorbed by the shield A.

A monochromatic luminous beam is thus emitted from the source within a narrow solid angle. The direction of radiation may be changed by adjusting a handle H. There are N different adjustments corresponding to N different depths of measurement, e.g. N=3, 6, 10, 15, 25, and 35. As illustrated in the Figure, the luminous beam is emitted into the material, the density of which should be determined. During the passage through the material, a portion of the gamma-quanta in the luminous beam will be scattered or absorbed. The scattered part is to a substantial degree dependent on the density of the scattered material.

When the radiation reaches the desirable depth of measurement it will be damped to a certain degree depending on the density of the material.

During the passage of the reflection volume V, a portion of the gamma-quanta is scattered away from the luminous beam depending on the density of the substance. A smaller portion of the radiation scattered in V will be directed towards the gamma-detector. On its way the radiation is damped further depending on the density of the material. The intensity of the radiation reaching the detector will thus depend strongly on the density (almost exponentially) of the object to be measured.

As mentioned the radiation of gamma-quanta away from the luminous beam during passage of a material depends on the density of the material. The dependency is the same for all materials, except materials containing hydrogen as well as heavy atoms. This is due to the fact that gamma-quanta are scattered by electrons, and the scattering probability is proportional to the electron density $N_e$ in the material. $N_e$ is indicated by the formula:

$$N_e = \frac{N_{Av}\rho Z}{A}$$

in which $N_{Av}$ is Avogadro's number, $\rho$ the density, Z the atom number, and A the mass number. Apart from hydrogen it applies for all not too heavy atoms that $Z/A \simeq 0.5$, for which reason N is proportional to $\rho$. For hydrogen it applies that $Z/A \simeq 1$. This involves that for water ($H_2O$)

$$\frac{Z}{A} = \frac{1+1+8}{1+1+16} = 0.55$$

i.e. 10% greater. In connection with gamma-radiation calculations it is thus necessary to correct for the abnormally great ability of water to scatter gamma-radiation by using in the calculations a corrected density of 1100 kg/m$^3$.

The radiation to be measured are the quanta of group A, which are scattered in the reflection volume V. The intensity of this radiation is substantially determined by the average density along the radiation path in the material.

The detector is provided with a collimator serving to filter off all gamma-radiation apart from the radiation having the correct direction, i.e. the direction from the reflection volume to the detector.

By means of shield and collimators the majority of the undesirable radiation is filtered off. It is, however, not possible by geometry alone to sort out all undesirable gamma-quanta. Quanta, which have been scattered twice or more (groups B and C), which do not reach far into the material, but which at the last scattering is directed up through the collimator of the detector (cf. FIG. 3), will also be detected, but they only contain information as to density down to the depth which they have reached.

The following method is used for measuring the quanta of group A alone.

Figure 3:
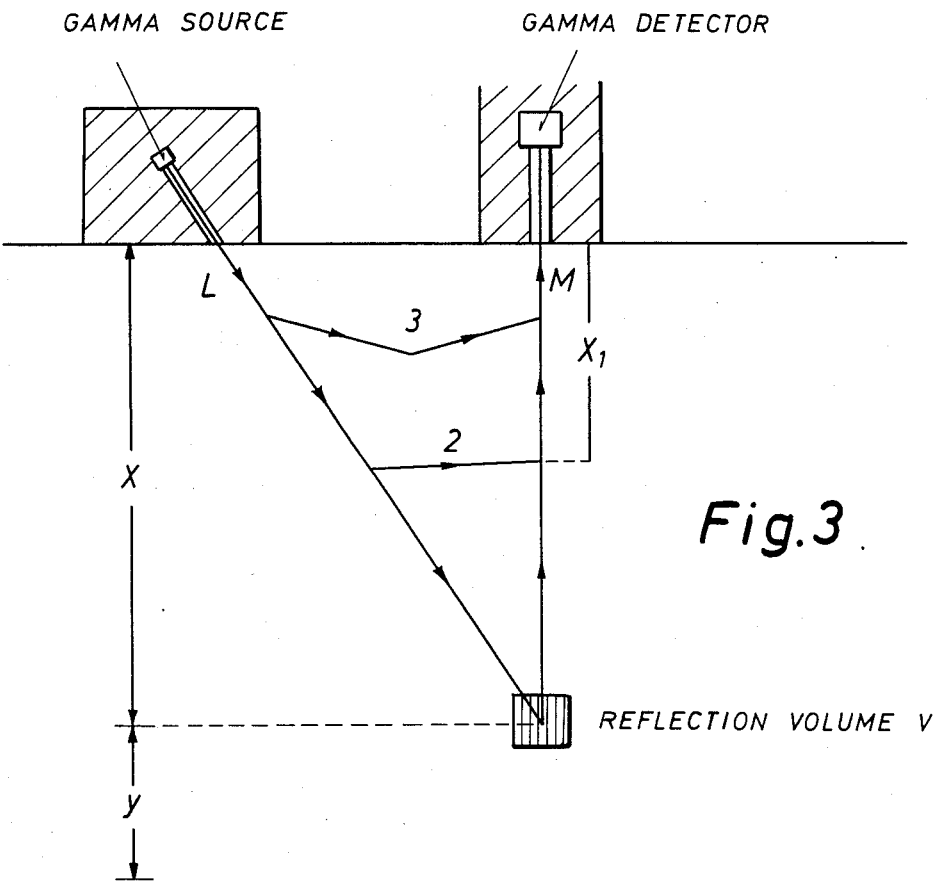
FIG. 3 is an illustration of the mode of operation of the measuring equipment illustrated in FIG. 2.

By the measuring arrangement illustrated in FIG. 3 a thin luminous beam L is emitted from the collimator of the source, said beam being damped exponentially during passage of the object under measurement.

This damping is substantially due to the Compton-scattering, by which the gamma-quanta are scattered away from the luminous beam L. As the quanta are emitted in all directions, some of them will be directed towards the detector. Due to the detector collimator only the quanta following the collimator line M will reach the detector and transmit a signal.

If the detector only detects quanta of group A the result of measurement will be an expression of the average density in the depth area from 0 to x.

An emitted gamma-quantum can, however, also follow the way L-2-M or L-3-M. These quanta are scattered more than once (here two and three times). If measurements were only performed on these quanta it is obvious that only information as to the density from 0 to $x_1$ will be obtained, and not as desired from 0 to x.

It can be illustrated that if the desired depth of measurement is less than about 10 cm, the majority of the measuring signal at normal densities and compositions will originate from quanta of group A. This is due to the slight probability of quanta of group B reaching the detector when subjected to two or more scatterings and thereafter ending in the correct direction.

When the depth of measurement x is increased, the fact that the signal from quanta of group A is damped exponentially, whereas the signal from quanta of groups B and C is almost constant, will soon lead to the detector signal being dominated by the signal from the undesirable quanta of groups B and C, which do not reach the desired depth.

By using Compton's formula on quanta of groups A and B it is illustrated that quanta of group B normally have more energy than the quanta of group A. The quanta of group C will normaly have considerably less energy.

Figure 4:
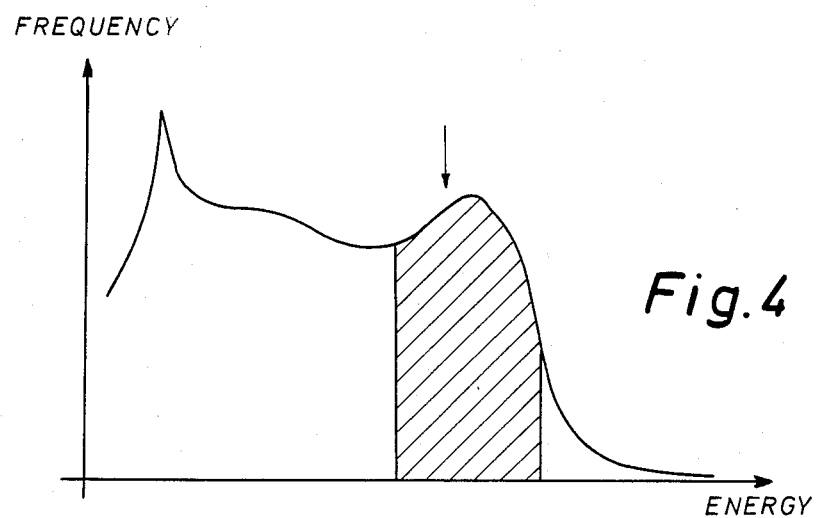
FIG. 4 illustrates the energy spectrum of the detected quanta.

A typical gamma-spectrum as registered by the detector is illustrated in FIG. 4. The part of the spectrum containing information as to the density from 0 to x is hatched. The arrow indicates the energy of the quanta of group A according to Compton's formula. It appears that the peak is displaced towards higher energies. This is due to the fact that the quanta of group B have energies in the same interval (somewhat higher) and actually drown the desired signal.

Figure 5:
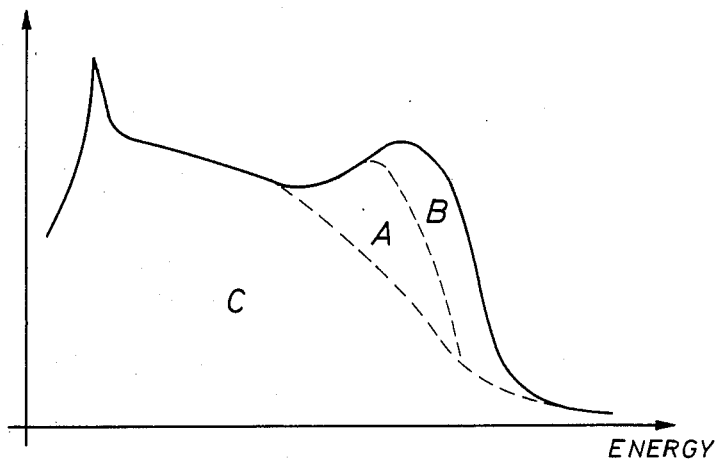
FIG. 5 illustrates the grouping of the quanta according to the number of scatterings.
Figure 6:
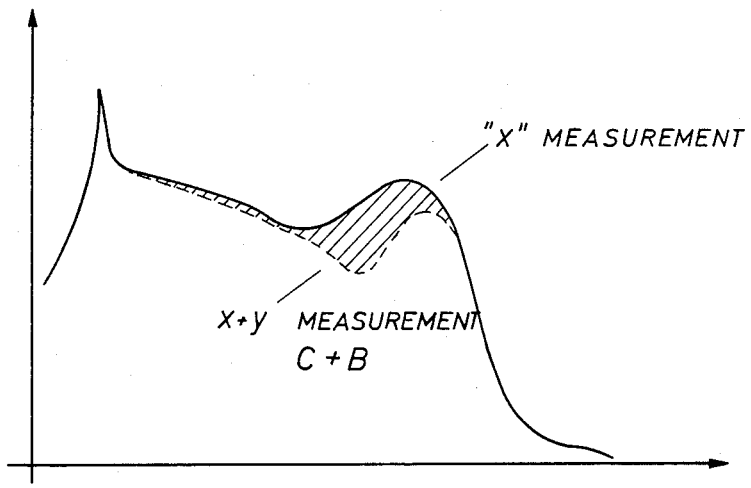
FIG. 6 is an illustration of how the spectrum may be analyzed by subtraction.

The spectrum of FIG. 4 may be understood as composed of three portions as illustrated in FIG. 5. The area A indicates the desired measuring signal from the quanta of group A. The area B indicates the signal from the quanta of group B (multiple scattering) and quanta of photo-electric emission in the detector collimator and from natural background radiation. By adopting two measurements, one having the depth of measurement x and one having the depth of measurement x+y, in which y is typically 10 cm, it is obtained that in the case where the depth of measurement is x+y the signal from the quanta of group A will in practice disappear, as the signal is damped during the passage of the further 2×10 cm. In x+y measurements the signal from the quanta of groups B and C will then on the other hand be practically unchanged as they move at considerably lower depth, and as their geometry is almost unchanged. As a result, by taking the difference between the results of the two measurements (x and x+y), a result of measurement is obtained merely determined by the quanta of group A (cf. FIG. 6), and on the basis hereof it is possible to determine the average density of the object of measurement from depth 0 to depth x.

SPECTRUM ANALYSIS OF THE RESULT OF MEASUREMENT

Out of a spectrum analysis of the peak A+B information is obtained as to the variation of the density with the depth at greater depths. This is also the case when adopting measurements of smaller depths.

In the following a spectrum analysis means an analysis of the shape of the spectrum originating from the measurement (energy-spectrum versus gamma-energy). FIG. 5 illustrates that the part of the spectrum, in which the area A is situated, is only partly congruent with the energy interval, within which the area B is situated. The average energy of the area B is higher than the average energy of the area A.

The number of countings in the area B depends on the average density in the depth interval from 0 to $x_1$ (cf. FIG. 3). Greater counting velocities within the area B are obtained in connection with a lower average density from 0 to $x_1$.

It is thus possible from the number of countings in the energy interval, in which B dominates, to calculate the average density from the depth 0 to $x_1$, $\rho(0-x_1)$ (cf. FIG. 4).

As described above the average density from the depth 0 to $x_1$, $\rho(0-x_1)$ may be determined by determination of the number of countings in the area A. On the basis of $\rho(0-x_1)$ and $\rho(0-x)$ the average density of the substratum in the depth $x_1$ to x, $\rho(x_1-x)$, may be determined by the formula $$\rho(x_1 - x) = \frac{\rho(0 - x)x - \rho(0 - x_1)x_1}{x - x_1}$$

On the basis of Compton's formula it can be illustrated that a gamma-quantum scattered as shown at "3" of FIG. 3 (three scatterings) will have a higher energy that a quantum scattered as shown at "2" of FIG. 3 (two scatterings). Both quanta will belong to the quanta of group B. It can be illustrated that the three times scattered quanta of group B detected have on the average obtained a smaller maximum depth than the corresponding twice scattered quanta. It generally applies that the N times scattered quanta reaching the detector will originate from a greater average depth than the N+1 times scattered quanta.

The signal originating from the quanta of group B can consequently be divided into energy intervals. The number of countings of each interval contains information as to the density down to a certain depth, and the higher the energy of the intervals is, the lower is the corresponding depth.

By dividing the energy area of the quanta of group B into a suitable number of intervals and analyzing the associated number of countings it is possible to calculate the average density in the corresponding depth intervals from the surface to the total depth of measurement.

By using the method of the least squares a suitably chosen function may be approximated to the gamma-spectrum of the quanta of group B. The values achieved of the adapter constants contain information as to the variation of the density with the depth. By means of the constants it is possible to estimate the density at a desirable depth, and the variation of the density with the depth can be calculated continuously.

The analyzing method here described is in practice applicable at all depths of measurement.

We claim:

1. A method of determining the density of substrata comprising:
    (a) irradiating the substrate by means of a directional gamma-ray radiation source and detecting the quanta of gamma-ray radiation backscattered from the substrata by a directional detector and by changing the direction of radiation relative to the direction of detection and measuring the change of the detected signal, the direction of radiation and the direction of detection being always in substantially the same plane;
    (b) counting the number of gamma rays received by the detector and providing a spectrum of counts versus energy of the detected gamma rays; and
    (c) determining the variation of the density with the depth of irradiation by calculating the average density in two depth intervals based on the countings in two energy intervals by utilizing the quanta backscattered a plurality of times, in which, the quanta backscattered N times being backscattered on average from a depth greater than the quanta backscattered N+1 times and the quanta backscattered N times having on average a different energy than the quanta backscattered N+1 times.

2. The method as claimed in claim 1 further including the steps of dividing the spectrum into three or more energy intervals and calculating the variation of the density with the depth in said three or more intervals.

* * * * *